US006855456B2

(12) United States Patent
Taylor et al.

(10) Patent No.: US 6,855,456 B2
(45) Date of Patent: Feb. 15, 2005

(54) TITANIUM ALLOY-PIN BATTERY FEEDTHROUGH FOR AN IMPLANTABLE MEDICAL DEVICE

(75) Inventors: William J. Taylor, Anoka, MN (US); Ian Courtney, St. Francis, MN (US); William G. Howard, Roseville, MN (US); Robert E. Kraska, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 226 days.

(21) Appl. No.: 10/003,925

(22) Filed: Oct. 30, 2001

(65) Prior Publication Data

US 2003/0083715 A1 May 1, 2003

(51) Int. Cl.[7] .................................................. H01M 2/02
(52) U.S. Cl. ....................... 429/181; 429/180; 429/184; 607/36; 607/37
(58) Field of Search ................ 607/36–37; 429/180–184

(56) References Cited

U.S. PATENT DOCUMENTS

| 4,180,700 A | 12/1979 | Kraska et al. ....... 174/152 GM |
|---|---|---|
| 4,212,930 A | 7/1980 | Athearn ...................... 429/101 |
| 4,225,262 A | 9/1980 | Koop et al. ................. 403/272 |
| 4,271,278 A | 6/1981 | Phillips et al. .............. 525/356 |
| 4,292,346 A | 9/1981 | Athearn ...................... 427/115 |
| 4,307,462 A | 12/1981 | Mazzocchi .................. 370/517 |
| 4,341,849 A | 7/1982 | Park et al. ................... 429/104 |
| 4,421,947 A | 12/1983 | Kyle .................... 174/152 GM |
| 4,514,207 A | * 4/1985 | Kyle ............................ 65/21.1 |
| 4,556,613 A | 12/1985 | Taylor et al. ............... 429/101 |
| 4,609,598 A | 9/1986 | Tucholski et al. .......... 429/174 |
| 4,678,868 A | 7/1987 | Kraska et al. ....... 174/152 GM |
| 5,015,530 A | 5/1991 | Brow et al. ................. 428/433 |
| 5,021,307 A | 6/1991 | Brow et al. ................. 429/184 |
| 5,137,849 A | 8/1992 | Brix et al. ..................... 501/15 |
| 5,175,067 A | 12/1992 | Taylor et al. ............... 429/181 |
| 5,821,011 A | * 10/1998 | Taylor et al. ............... 429/181 |
| 2001/0055716 A1 | * 12/2001 | Frysz et al. ................. 429/184 |
| 2002/0155350 A1 | * 10/2002 | Spillman .................... 429/181 |

FOREIGN PATENT DOCUMENTS

EP          0 269 007       11/1987       ............ A61N/1/36

OTHER PUBLICATIONS

Rhee, S.K., "Wetting of Ceramics by Liquid Metals", Journal of Am. Ceramic Soc., pp. 332–334, 1971.
Appeal No. 91–2506 On Brief, Board of Patent Appeals & Interferences, United States Patent and Trademark Office, pp. 1–8.
Watkins, R.D., "Development of CABAL Glasses for Use in Lithium Ambient–Temperature Batteries", Abstract, SAND–87–0393, 1987.
Watkins, R.D., "Corrosion Resistant Glasses for Use in Lithium Ambient–Temperature Batteries", Abstract from Proc. Intersoc. Energy Covers. Eng. Conference, 1987.
Brow, Richard K., Reactions & Bonding Between Glasses & Titanium, SAND–87–0541C, DE88–00603, 1987.

* cited by examiner

Primary Examiner—Carl Layno
(74) Attorney, Agent, or Firm—Paul H. McDowall; Girma Wolde-Michael (57) ABSTRACT

A feedthrough arrangement includes a titanium alloy terminal for conducting electrical current between a first environment within a housing and a second environment outside of the housing. An insulating member is positioned around a portion of the terminal. A sleeve member is positioned around the insulating member. The terminal, insulating member, and insulating member all being in sealing engagement therewith to environmentally isolate the first and second environments.

36 Claims, 5 Drawing Sheets

TITANIUM ALLOY-PIN BATTERY FEEDTHROUGH FOR AN IMPLANTABLE MEDICAL DEVICE

FIELD OF THE INVENTION

This invention relates generally to sealed devices, and, more particularly, to an implantable medical device that utilizes a battery incorporating a glass-to-metal feedthrough with a titanium alloy feedthrough pin.

DESCRIPTION OF THE RELATED ART

Since their earliest inception some forty years ago, there has been a significant advancement in body-implantable electronic medical devices. Today, these implantable devices include therapeutic and diagnostic devices, such as pacemakers, cardioverters, defibrillators, neurological brain and muscle stimulators, drug administering devices, among others for alleviating the adverse effects of various health ailments. Today's implantable medical devices are also vastly more sophisticated and complex than their predecessors, and are therefore capable of performing considerably more complex tasks for reducing the effects of these health ailments.

Usually, body-implantable medical devices rely on battery power to perform their therapeutic and/or diagnostic tasks. The battery supplies power to the electrical components of the implantable medical device and may also be used to charge a capacitor, which is capable of delivering a therapeutic "shock" to the heart to regulate the heart's rhythm, for example.

Typically, the battery includes corrosive materials that may undesirably damage the other electrical components of the implantable medical device. As a result, the battery is typically configured with an electrical feedthrough arrangement. The feedthrough arrangement enables electrical connection between the battery and the other electrical components of the implantable medical device, while maintaining environmental isolation between the corrosive materials within the battery and the other electrical components within the device. Some of the sealing materials used for the feedthrough arrangement tend to have less corrosion resistance than others, and, consequently, may enable some of the corrosive material to escape from the battery.

Any leakage of the corrosive material from the battery to the other electrical components within the implantable medical device may cause the device to function improperly or otherwise cause it to cease operating altogether. In addition, because the medical device is surgically implanted within the patient's body, accessibility to the device is difficult for repair or replacement subsequent to implantation. If the implantable medical device functions improperly or fails altogether as a result of the leakage of the corrosive material, it may prove fatal to the patient. Moreover, if the corrosive material of the battery leaks into the housing of the implantable medical device, it may increase the likelihood that the material may leak into the patient's body, thus causing injury or fatality.

The present invention is directed to overcoming, or at least reducing the effects of, one or more of the problems set forth above.

SUMMARY OF THE INVENTION

In one aspect of the present invention, a feedthrough arrangement is provided. The feedthrough arrangement comprises a terminal for conducting electrical current, where the terminal comprises a titanium alloy. An insulating member is positioned around a portion of the terminal and is in sealing engagement therewith. A sleeve member is positioned around the insulating member and is in sealing engagement with the insulating member.

In another aspect of the present invention, a housing is provided. The housing has an opening and establishes a first environment within the housing. The housing comprises a feedthrough arrangement including a titanium alloy terminal for conducting electrical current between the first environment within the housing and a second environment outside of the housing. The feedthrough arrangement further includes an insulating member positioned around a portion of the terminal and in sealing engagement therewith. A sleeve member is positioned around the insulating member and is in sealing engagement with the insulating member. The sleeve member is coupled to the housing at the opening thereof.

In another aspect of the invention, a method is provided. The method provides environmental isolation between a first environment within a housing and a second environment outside of the housing. The method includes providing a titanium alloy terminal for conducting electrical current between the first environment and the second environment. An insulating member is provided and positioned around a portion of the terminal and in sealing engagement therewith. A sleeve member is also provided and positioned around the insulating member and in sealing engagement with the insulating member, the sleeve member being coupled to the housing at an opening thereof.

In another aspect of the invention, an apparatus is provided. The apparatus comprises a titanium alloy terminal for conducting electrical current between a first space within a container and a second space outside of the container. An insulating member is positioned around a portion of the terminal and is in sealing engagement therewith. A sleeve member is positioned around the insulating member and is in sealing engagement with the insulating member. The sleeve member and insulating member isolates the first and second spaces.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
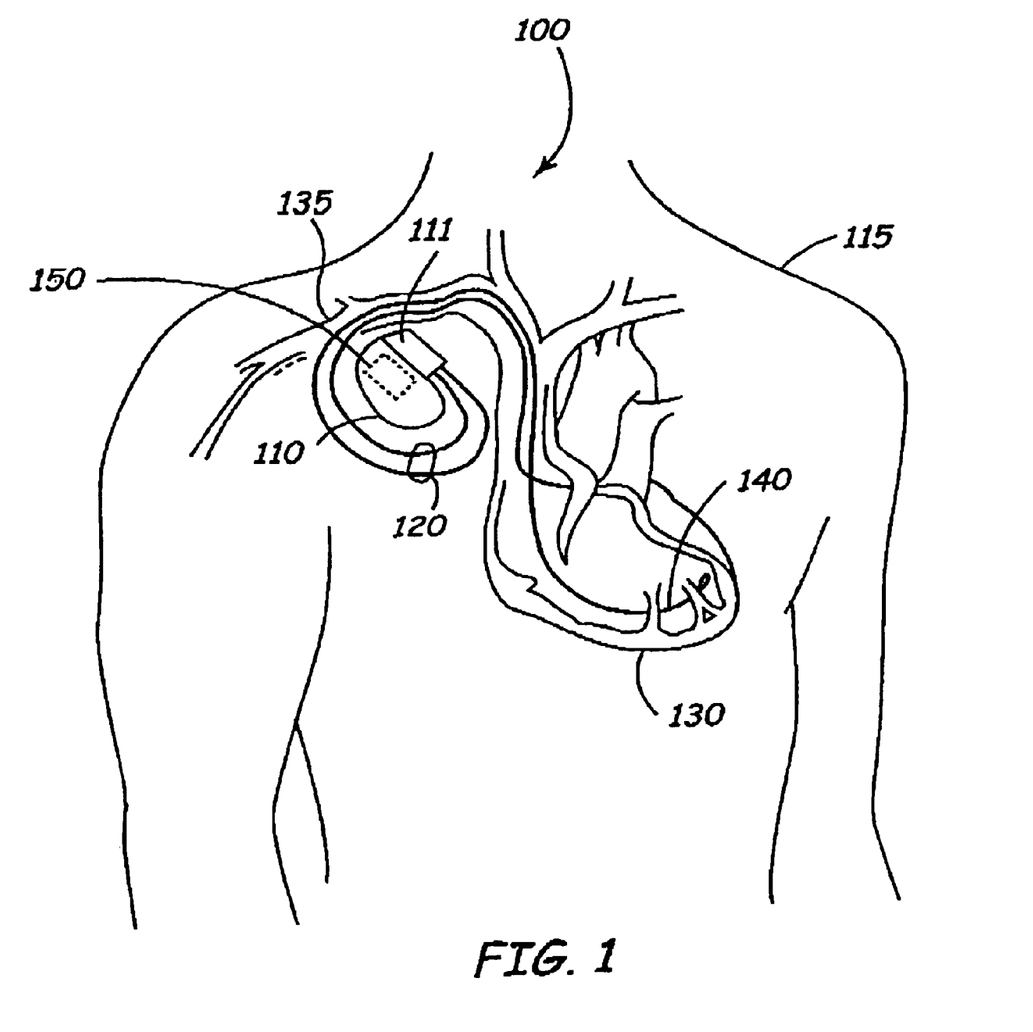
FIG. 1 schematically illustrates one embodiment of an implanted medical device in the form of a pacemaker and associated leads positioned to stimulate and/or sense the heart.

Turning now to the drawings, and specifically referring to FIG. 1, an implantable medical device (IMD) system 100 is shown in accordance with one embodiment of the present invention. The IMD system 100 includes an implantable electronic device 110 that has been implanted in a patient 115. In accordance with one embodiment, the device 110 may take the form of a pacemaker, cardioverter, defibrillator, neurological brain or muscle stimulator or drug administering device. It will be appreciated, however, that this list of examples is not exhaustive, and, thus, the implantable device 110 may take the form of a variety of other devices without departing from the spirit and scope of the present invention.

The device 110 is housed within a hermetically sealed, biologically inert outer housing or container, which may itself be conductive so as to serve as an electrode in the pacemaker's pacing/sensing circuit. One or more pacemaker leads, which are collectively identified by reference numeral 120, are electrically coupled to the device 110 in a conventional manner and extend into the patient's heart 130 through a cardiac vessel 135, such as a vein. Disposed generally near a distal end of the leads 120 are one or more exposed conductive electrodes 140 for sensing cardiac activity, delivering electrical pacing stimuli (i.e., therapeutic signals) to the heart 130, or providing a stimulating voltage to defibrillate the heart 130. The leads 120 may be implanted with their distal end situated adjacent the atrium or the ventricle, or both, of the heart 130. A battery 150, which is an integral part of the implantable device 110, provides power thereto.

Figure 2:
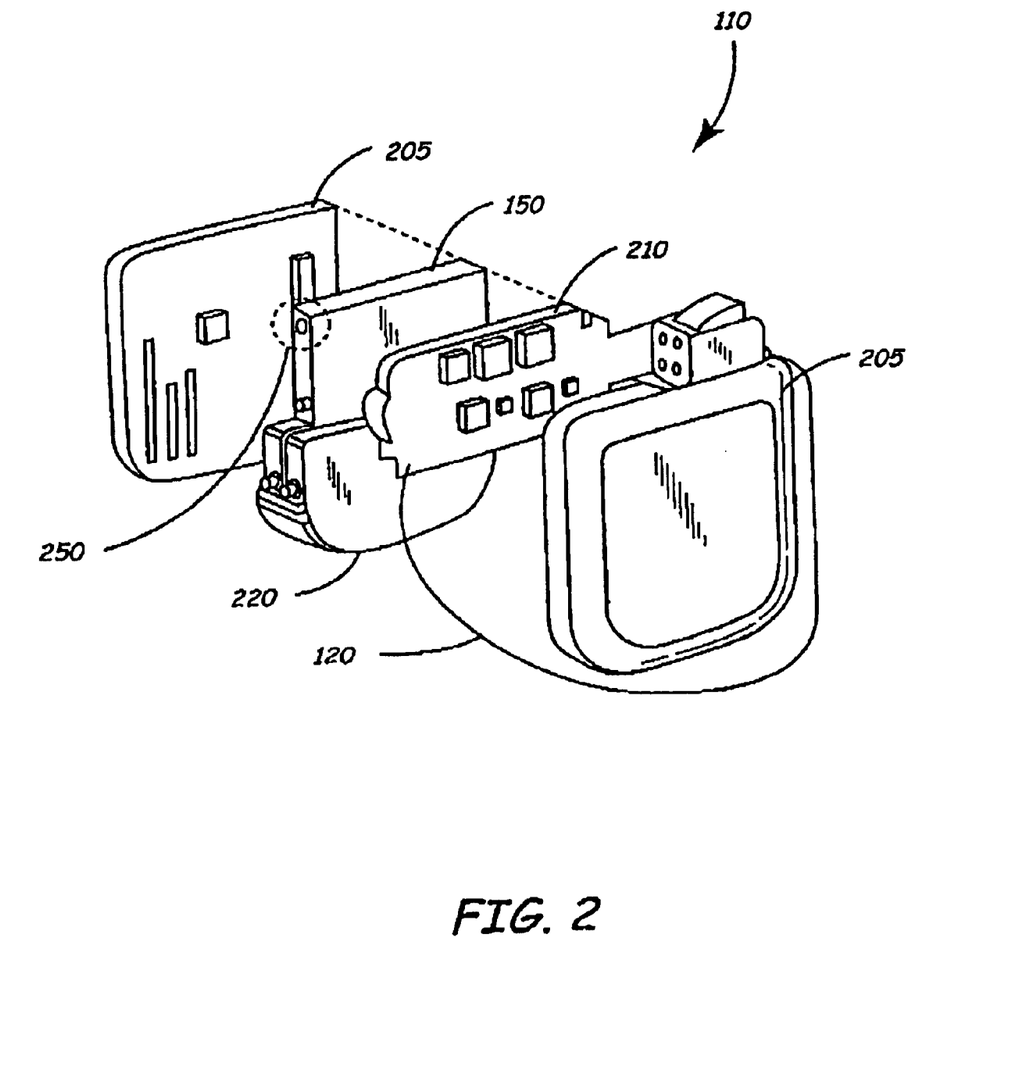
FIG. 2 provides a three-dimensional, multi-layered view of an implantable medical device for surgical implantation within a patient's body in accordance with one embodiment of the present invention.

Turning now to FIG. 2, a three-dimensional, multi-layered view of the electronic device 110 is shown in accordance with one embodiment of the present invention. The device 110 is contained within a hermetically sealed, biologically inert housing 205 to protect the device 110 from body fluids within the patient's body 115 in which the device 110 has been surgically implanted.

The housing 205 includes a processor unit 210, the battery 150, and a capacitor package 220. In the illustrated embodiment, the processor unit 210 may be configured to record diagnostic signals received via the conductive electrodes 140 located at the distal end of the leads 120. In response to the diagnostic signals received, the processor unit 210 may be configured to administer therapeutic signals to the patient's heart by releasing energy stored within the capacitor package 220, and directing the energy along the leads 120 to the patient's heart 130.

The battery 150 provides power to the processor unit 210 for the operation of the various electrical components of the device 110. In one embodiment, a therapy may be delivered to a portion of the patient's body 115 by releasing the charge from the capacitor package 220 within a short period of time. The battery 150 provides the energy required to charge the capacitor package 220. According to the illustrated embodiment, the battery 150 may take the form of a rechargeable (secondary) lithium-ion battery, which may incorporate a negative active material comprised of Carbon, a positive active material of a lithium transition metal oxide, such as $LiCoO_2$, for example, and a lithium containing salt, such as $LiPF_6$ and an appropriate organic solvent for the $LiPF_6$ salt, for example. In an alternative embodiment, the battery 150 may be provided as a primary lithium battery. It will also be appreciated that the battery 150 may take the form of various other battery types or electrochemical cells, and, thus need not necessarily be limited to the aforementioned examples.

In accordance with the illustrated embodiment, the battery 150 is configured with a feedthrough arrangement 250. The feedthrough 250 enables the transmission of electrical current between the environment within the battery 150 and the environment outside of the battery 150, while maintaining electrical and environmental isolation between the two environments. Typically, the battery 150 includes corrosive materials that may undesirably damage the other components of the device 110, such as the processor unit 210, for example. Any leakage of the corrosive material from the battery 150 to other components within the implantable device 110 may cause it to function improperly or otherwise cause it to cease operating altogether. In addition, because the device 110 is surgically implanted within the patient's body, its accessibility may be difficult for repair or replacement subsequent to implantation. Accordingly, the feedthrough arrangement 250 is designed to prevent leakage of corrosive materials from the battery 150 while permitting electrical current to be exchanged between the battery 150 and the other components of the implantable device 110. Thus, the likelihood of any potential damage that may result from the corrosive material to the components of the device 110 may be reduced, if not eliminated, by the feedthrough arrangement 250 of the present invention.

Figure 3:
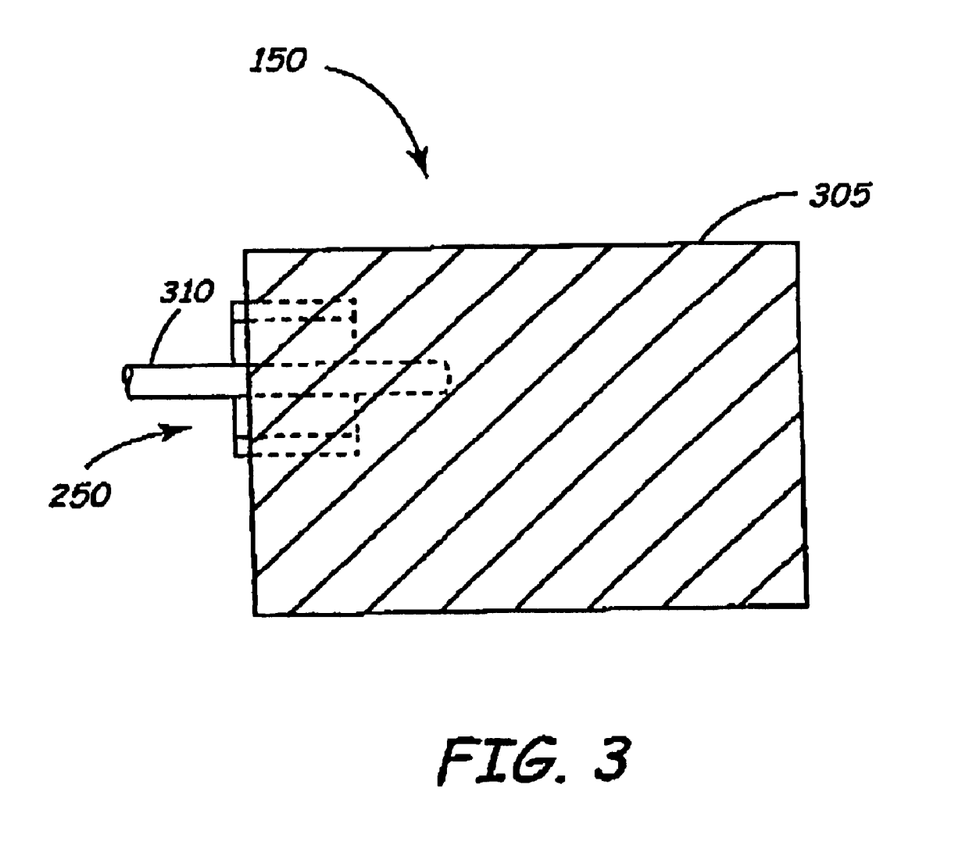
FIG. 3 shows a more detailed representation of a battery with a feedthrough within the implantable medical device of FIG. 2 according to one embodiment.

Turning now to FIG. 3, a more detailed representation of the battery 150 is shown in accordance with one embodiment of the present invention. The battery 150 includes a housing 305 for encapsulating its components, which may include corrosive material therein. In accordance with one embodiment, the housing 305 is constructed of stainless steel, such as 304L stainless steel. It will be appreciated, however, that the housing 305 may be constructed from various other metals or materials without departing from the spirit and scope of the present invention.

The battery 150 is further configured with a center pin or terminal 310, which permits electrical conduction between the inside and outside environments of the battery housing 305, while creating a hermetic seal with the housing 305. For illustrative purposes, the dotted line portion of the feedthrough arrangement 250 is shown to reside within the housing 305. It will be appreciated that the location of the feedthrough arrangement 250 on the battery housing 305 may vary depending on the specific design of the battery 150. Accordingly, the location of the feedthrough arrangement 250 on the battery housing 305 need not necessarily be limited to the particular location shown in FIG. 3.

Figure 4:
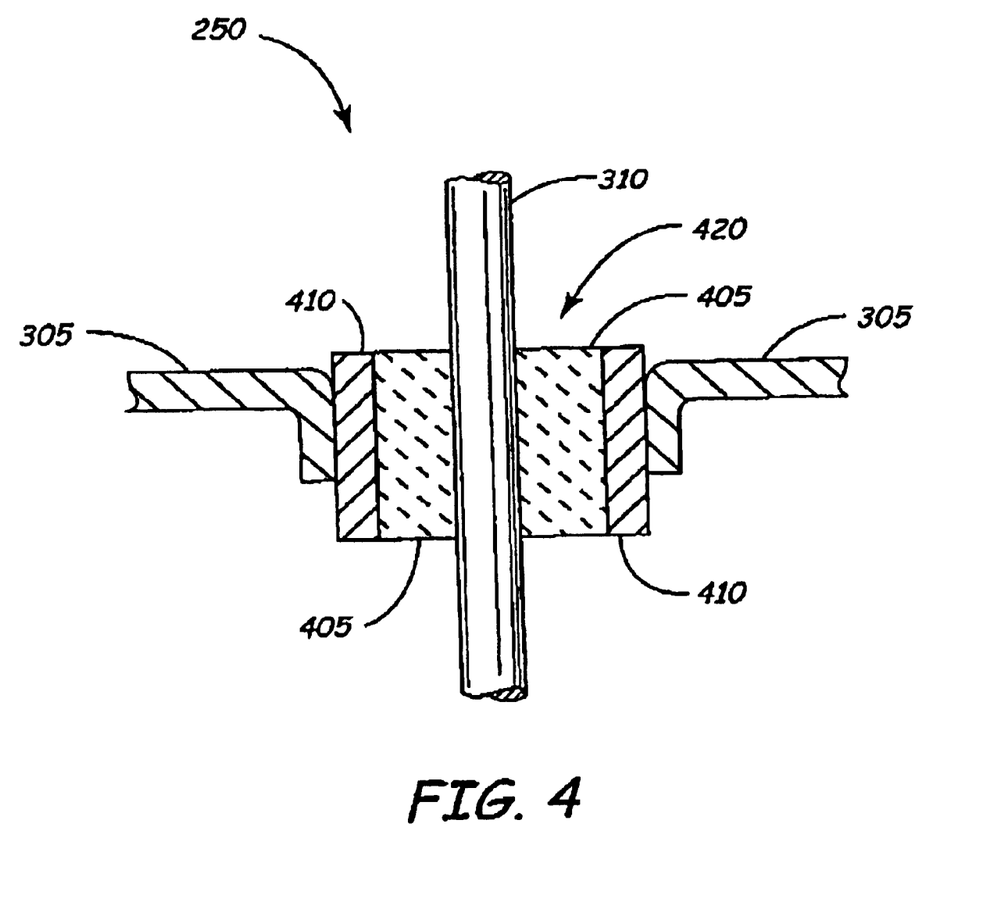
FIG. 4 shows a cross-sectional view of a feedthrough arrangement for the battery of FIG. 3 in accordance with one embodiment of the present invention.

Turning now to FIG. 4, a cross-sectional view of a more detailed representation of the feedthrough arrangement 250 for the battery 150 is shown in accordance with the illustrated embodiment. The feedthrough arrangement 250 comprises the center pin or terminal 310, a glass seal member 405, and a ferrule sleeve 410, which are disposed within an opening 420 of the battery housing 305. The center pin 310 enables an electrical conduction between the inside and outside environments of the battery housing 305, while creating a hermetic seal with the glass seal member 405. The hermetic seal is provided to prevent any leakage of corrosive material from escaping the battery housing 305. In the illustrated embodiment, the center pin 310 functions as the positive current collector for the battery 150 and the ferrule sleeve 410 functions as the negative current collector.

Although the feedthrough arrangement 250 of the present invention is described for use with the battery 150 of the implantable device 110, its application is not so limited. It will be appreciated that the feedthrough arrangement 250 may apply to various other types of housings in which it is desirable to provide a hermetically sealed electrical connection between the inner and outer portions of a housing. Therefore, it will be appreciated that the feedthrough arrangement 250 as disclosed need not necessarily be limited for use with battery housings or even medical devices.

According to the illustrated embodiment of the present invention, the battery housing 305 and the ferrule sleeve 410 are constructed of the same material, which may be 304L stainless steel in one embodiment. It will be appreciated, however, that the battery housing 305 and the ferrule sleeve 410 may be constructed of various other types of stainless steel, other types of metals or other materials without departing from the spirit and scope of the present invention. For example, the battery housing 305 and ferrule sleeve 410 may be constructed from titanium or a titanium alloy. In the illustrated embodiment, the ferrule sleeve 410, which takes the form of a cylindrical shape, is welded to the battery housing 305 at the opening designated at 420. It will be appreciated that the ferrule sleeve 410 need not necessarily be limited to the shape of a cylinder, but may take the form of other suitable shapes for contacting with the battery housing 305. In the illustrated embodiment, the ferrule sleeve 410 and the battery housing 305 function as the negative current collector of the battery 150.

The center pin or terminal 310 extends through the opening 420 of the battery housing 305, thereby permitting the transmission of electrical current between the environment inside the battery housing 305 and the environment outside the housing 305. The center pin 310 functions as the positive current collector for the battery 150 and is in sealing engagement with the glass seal member 405. According to the illustrated embodiment, the center pin 310 is constructed of an aluminum containing titanium alloy. For example, in one embodiment, the center pin 310 may be constructed of Ti-6Aluminum-4Vanadium. Alternatively, the center pin 310 may be constructed from Ti-6Aluminum-4Vanadium ELI (Extra Low Interstitial) or Ti-3Aluminum-2.5Vanadium. Aluminum containing titanium alloys tend to be less prone to the corrosive effects of the material contained within the battery housing 305. Accordingly, when aluminum containing titanium alloys are used for the center pin 310, the likelihood of the pin 310 corroding is reduced, and thus, the likelihood of the corrosive materials escaping from the battery housing 305 is reduced as well. It will be appreciated that the center pin 310 may also be constructed from compositions of titanium alloy other than the examples provided above.

In accordance with one embodiment of the present invention, the glass seal member 405 of the feedthrough arrangement 250 may take the form of a boro-aluminate glass, such as Cabal-12 glass, for example. Cabal-12 glass has a thermal expansion of approximately $6.8 \times 10^6$ in/in/° C., and includes the following concentration in mole percentage oxide: $B_2O_3$ 40.0, $Al_2O_3$ 20.0, MgO 20.0 and CaO 20.0. It will be appreciated, however, that the glass seal member 210 may also include variations of Cabal-12 glass or various other types of glass suitable for sealing the feedthrough arrangement 250 of the battery housing 305.

Figure 5:
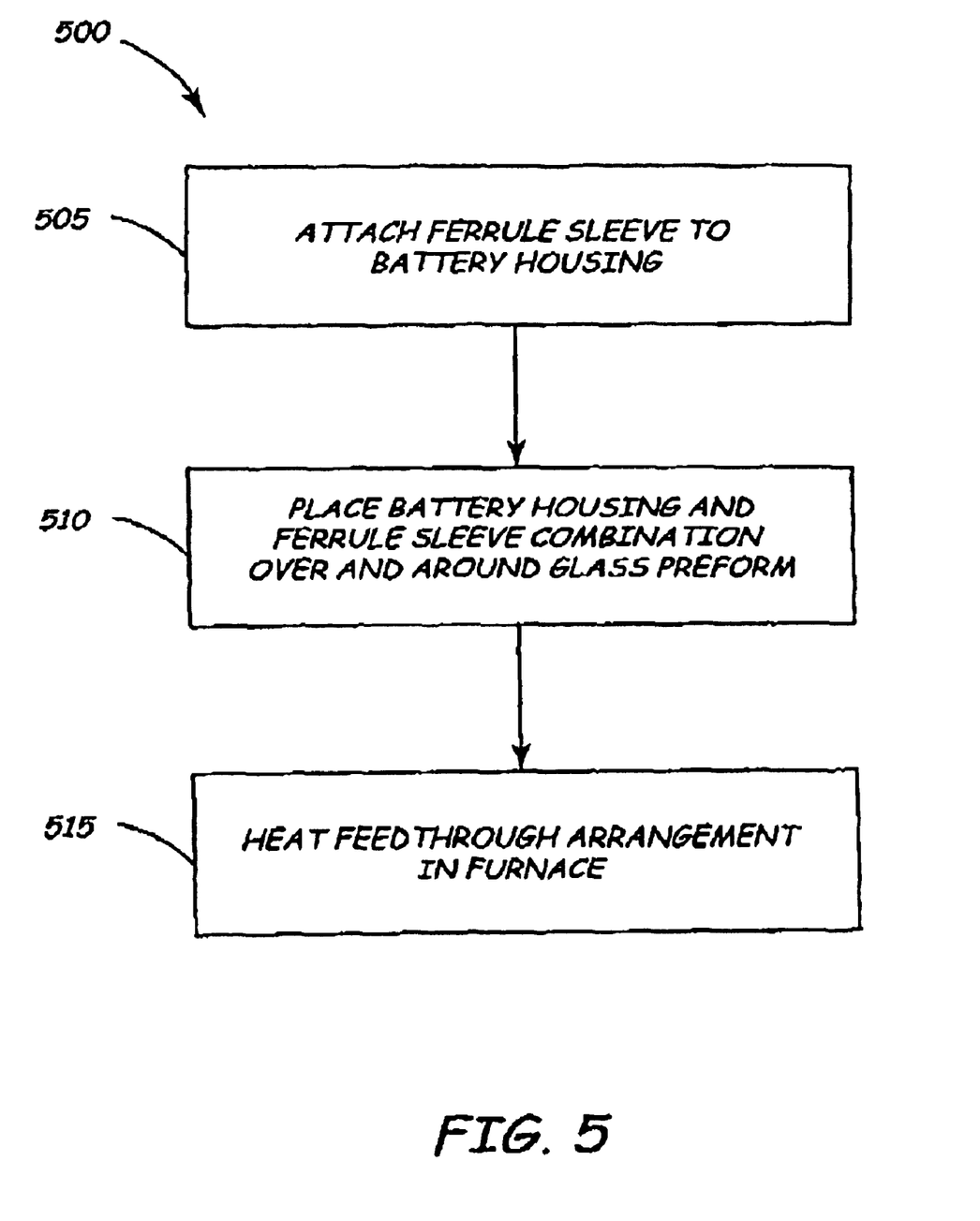
FIG. 5 shows a process for implementing the feedthrough arrangement of the battery in accordance with one embodiment of the present invention.

Turning now to FIG. 5, a process 500 for implementing the feedthrough arrangement 250 on the battery housing 305 is shown according to one embodiment of the present invention. The process 500 commences at block 505 where the ferrule sleeve 410 may be welded to the battery housing 305 at the opening designated at 420. At block 510, the battery housing 305, along with the ferrule sleeve 410 welded thereto, is placed over and around a glass preform of Cabal-12 glass, which forms the glass seal member 405 when heated in a furnace. The glass preform is positioned around the center pin 310 and the entire assembly is placed on or in a high purity graphite fixture to insure the proper location of the components of the feedthrough arrangement 250. High purity graphite is typically used as the fixture material during the seal formation due to its thermal conductivity, long service life at high temperatures and passivity to the sealing glass, thereby reducing the likelihood of adhesion of the glass preform to the fixture material.

The feedthrough arrangement 250 is then heated in a furnace at block 515. In one embodiment, the sealing of the feedthrough arrangement 250 may be accomplished at approximately 800° C. in an atmosphere consisting of high purity argon gas. During the heating process, the Cabal-12 glass preform melts and engages the center pin 310 and the ferrule sleeve 410, thereby forming the glass seal member 405. The glass seal member 405 provides a hermetic seal between the center pin 310 and the ferrule sleeve 410. Due to the high viscosity of the sealing glass preform, mechanical deformation of the sealing glass preform may be used to promote uniform contact with the center pin 310 and the ferrule sleeve 410 by the sealing glass member 405 as the glass reaches its melting point. This may be accomplished by positioning a high purity graphite cylinder (not shown) over the center pin 310 until it engages the sealing glass preform surface. Additionally, a forming weight cylinder (not shown) of high density material (such as tantalum, for example) may be positioned over and around the center pin 310 until it engages the graphite cylinder. In one embodiment, both of these cylinders are added to the feedthrough arrangement 250, which is contained and secured by a high purity graphite base fixture prior to creation of the glass-to-metal seal at the melting temperature. The center pin 310 may be used as a guide to insure the proper alignment of the components of the feedthrough arrangement 250 during the sealing process. The forming weight cylinder supplies a mass sufficient to compress the sealing glass 405 in a substantially uniform manner. The graphite sleeve may act as a removable parting sleeve after the creation of the hermetic seal by the glass seal member 405. The hermetic seal may be formed by virtue of the ferrule sleeve 410 having a thermal contraction rate greater than that of the glass seal member 405 and the center pin 310 upon cooling and/or the formation of a reaction layer between the sleeve 410 and the glass 405 resulting in the chemical adhesion of the two components.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A feedthrough arrangement, comprising:
a titanium alloy terminal for conducting electrical current;
an insulating member positioned around a portion of the terminal, the insulating member being in sealing engagement therewith; and
a sleeve member positioned around the insulating member, the sleeve member being in sealing engagement with the insulating member.

2. The feedthrough arrangement of claim 1, wherein the terminal comprises at least one of Ti-6Al-4V, Ti-6Al-4V ELI (extra low interstitial), and Ti-3Al-2.5V.

3. The feedthrough arrangement of claim 1, wherein the insulating member comprises glass.

4. The feedthrough arrangement of claim 3, wherein the glass comprises Cabal-12 glass.

5. The feedthrough arrangement of claim 4, wherein the Cabal-12 glass comprises about 40.0 mole % $B_2O_3$, 20.0 mole % $Al_2O_3$, 20.0 mole % MgO and 20.0 mole % CaO.

6. The feedthrough arrangement of claim 1, further comprising:
a housing having an opening, the sleeve member being coupled to the housing at the opening, and the housing comprising a first environment within; and
wherein the terminal extends from the first environment within the housing to a second environment outside of the housing.

7. The feedthrough arrangement of claim 6, wherein the terminal conducts electrical current between the first environment and the second environment and the glass seal member provides isolation between the first and second environments.

8. The feedthrough arrangement of claim 6, wherein the sleeve member is welded to the housing at the opening of the housing.

9. The feedthrough arrangement of claim 6, wherein the housing and sleeve member comprise stainless steel.

10. The feedthrough arrangement of claim 9, wherein the housing and sleeve member comprise 304L stainless steel.

11. The feedthrough arrangement of claim 6, wherein the housing comprises an electrochemical cell.

12. The feedthrough arrangement of claim 6, wherein the housing comprises a battery.

13. The feedthrough arrangement of claim 12, wherein the battery comprises a lithium-ion battery.

14. The feedthrough arrangement of claim 6, wherein the housing is a component of an implantable medical device.

15. The feedthrough arrangement of claim 14, wherein the implantable medical device comprises at least one of a pacemaker, cardioverter, defibrillator, neurological muscle or brain stimulator, and a drug administering device.

16. A housing having an opening and including a first environment within the housing, comprising:
a feedthrough arrangement, wherein the feedthrough arrangement includes:
a titanium alloy terminal for conducting electrical current between the first environment within the housing and a second environment outside of the housing;
an insulating member positioned around a portion of the terminal and in sealing engagement therewith; and
a sleeve member positioned around the insulating member and in sealing engagement with the insulating member, the sleeve member being coupled to the housing at the opening thereof.

17. The housing of claim 16, wherein the titanium alloy terminal comprises at least one of Ti-6Al-4V, Ti-6Al-4V ELI (extra low interstitial), and Ti-3Al-2.5V.

18. The housing of claim 16, wherein the insulating member comprises glass.

19. The housing of claim 18, wherein the glass comprises Cabal-12 glass.

20. The housing of claim 19, wherein the Cabal-12 glass comprises about 40.0 mole % $B_2O_3$, 20.0 mole % $Al_2O_3$, 20.0 mole % MgO and 20.0 mole % CaO.

21. The housing of claim 16, wherein the sleeve member is welded to the housing at the opening of the housing.

22. The housing of claim 16, wherein the housing and sleeve member comprise stainless steel.

23. The housing of claim 22, wherein the housing and sleeve member comprise 304L stainless steel.

24. The housing of claim 16, wherein the housing comprises an electrochemical cell.

25. The housing of claim 16, wherein the housing comprises a battery.

26. The housing of claim 25, wherein the battery comprises a lithium-ion battery.

27. The housing of claim 16, wherein the housing is a component of an implantable medical device.

28. The housing of claim 27, wherein the implantable medical device comprises at least one of a pacemaker, cardioverter, defibrillator, neurological muscle or brain stimulator, and a drug administering device.

29. A method for providing environmental isolation between a first environment within a housing and a second environment outside of the housing, comprising:
providing a titanium alloy terminal for conducting electrical current between the first environment and the second environment;
providing an insulating member positioned around a portion of the terminal and in sealing engagement therewith; and
providing a sleeve member positioned around the insulating member and in sealing engagement with the insulating member, the sleeve member being coupled to the housing at an opening thereof.

30. The method of claim 29, wherein providing an insulating member further comprises:
providing a Cabal-12 glass member positioned around a portion of the terminal and in sealing engagement therewith.

31. The method of claim 29, wherein providing a titanium alloy terminal further comprises:
providing a titanium alloy terminal for conducting electrical current between the first environment and the second environment, the titanium alloy terminal including one of Ti-6Al-4V, Ti-6Al-4V ELI (extra low interstitial), and Ti-3Al-2.5V.

32. The method of claim 29, wherein the housing comprises a battery.

33. An apparatus, comprising:
a titanium alloy terminal for conducting electrical current between a first space within a container and a second space outside of the container;
an insulating member positioned around a portion of the terminal and in sealing engagement therewith; and a sleeve member positioned around the insulating member and in sealing engagement with the insulating member;

wherein the insulating member isolates the first and second spaces.

34. The apparatus of claim 33, wherein the titanium alloy terminal comprises at least one of Ti-6Al-4V, Ti-6Al-4V ELI (extra low interstitial), and Ti-3Al-2.5V.

35. The apparatus of claim 33, wherein the insulating member comprises Cabal-12 glass.

36. The apparatus of claim 33, wherein the container encases a battery.

* * * * *